United States Patent [19]
Pye et al.

[11] Patent Number: 5,374,992
[45] Date of Patent: Dec. 20, 1994

[54] EXHAUST GAS PARTICLE SENSOR

[75] Inventors: John A. Pye; Nicholas J. Archer, both of Essex, United Kingdom

[73] Assignee: GEC-Marconi Limited, Middlesex, United Kingdom

[21] Appl. No.: 963,493

[22] Filed: Oct. 20, 1992

[30] Foreign Application Priority Data

Oct. 22, 1991 [GB] United Kingdom ............... 9122375

[51] Int. Cl.$^5$ ............................................. G01N 21/61
[52] U.S. Cl. ............................ 356/439; 356/440; 359/509
[58] Field of Search ............... 356/246, 438, 439, 440, 356/437; 250/576, 343; 359/509

[56] References Cited

U.S. PATENT DOCUMENTS 3,833,305 9/1974 Porter et al. .................. 356/438
4,277,131 7/1981 Hart et al. ..................... 356/439
4,413,911 11/1983 Rice et al. ..................... 356/438

FOREIGN PATENT DOCUMENTS 1329995 9/1973 United Kingdom .

*Primary Examiner*—Richard A. Rosenberger
*Attorney, Agent, or Firm*—Lowe, Price, LeBlanc & Becker

[57] ABSTRACT

An exhaust gas particle sensor has an inlet tube and a sensing region having different cross sections and linked by a transition region including a number of baffles arranged so that the time taken for gas to travel from the inlet tube to the sensing region is substantially independent of the position of the gas across the inlet tube. The sensor operates by measuring the opacity of the exhaust gas using a light beam which passes in and out of the sensing region through windows, the exhaust gas being prevented from impinging on each window by a double air curtain.

9 Claims, 4 Drawing Sheets

EXHAUST GAS PARTICLE SENSOR

BACKGROUND OF THE INVENTION

This invention relates to an exhaust gas particle sensor and in particular to a vehicle exhaust smoke sensor.

Increasingly legislation is being enacted to set limits on vehicle exhaust smoke, particularly from diesel engined vehicles.

It has been proposed in our co-pending patent application No. 9105731 that levels of smoke or other particles in vehicle exhausts could be sensed by measuring the opacity of the exhaust gases.

The opacity is measured by passing a light beam across a chamber through which the exhaust gases are flowing and measuring the reduction in the intensity of the light beam after its passage through the chamber.

For compression ignition engines, also known as diesel engines, the current UK exhaust smoke limit is defined as an absorption coefficient of $3.2 \text{ m}^{-1}$.

In practice a number of problems have been encountered with this approach. Firstly, it is desirable to have the optical path length through the chamber of adequate length in order to obtain the optimum change in light beam intensity for a given opacity. However it has been found that where the size or shape of the chamber is different to that of the pick-up or inlet tube collecting exhaust gases the maximum measured opacity, or peak opacity, tends to be less than expected Secondly, in order to prevent sooting up of the windows by deposition from the exhaust gases, clean air has been used to prevent the exhaust gases coming into contact with the windows through which the light beam enters and leaves the chamber. It has been found that the use of such air can produce erratic opacity measurements.

This invention was made in an attempt to produce an exhaust gas particle sensor at least partially overcoming these problems.

BRIEF SUMMARY OF THE INVENTION

In a first embodiment this invention provides an exhaust gas particle sensor comprising an inlet section, a transition section and an opacity measurement section in gas flow series, the measurement section having a different cross section to the inlet section and including a number of first baffles arranged such that the time taken for gas to travel from the inlet section to the measurement section is substantially independent of the position of the gas across the inlet section By different cross section it is meant that the cross sectional area or shape or both may be different.

It has been realised that the observed reduction in peak opacity where the cross sectional area or shape of the measurement section is different to that of the inlet section is caused by some regions in the exhaust gas traveling faster than others due to the change of cross section. For example, where the inlet section has a smaller cross sectional area than the measurement section the gases at the centre of the inlet section will generally flow faster into the measurement section than the gases nearer the sides.

As a result, a wavefront, such as a pulse or puff of more dense smoke in the exhaust gases in the inlet section, will become spread out along the length of the measurement section. As a result the wavefront or pulse of dense smoke will be spread out in time as it passes an opacity measuring element in the measurement section. This process causes peaks of high opacity to be averaged out and the measured peak opacity to be reduced.

The provision of baffles to make the gas exhaust travel time independent of position across the inlet section removes this source of error.

In a second embodiment this invention provides an exhaust gas particle sensor including a measurement section where the sensor can measure the opacity of the exhaust gas along an optical path which passes through a transparent window and the exhaust gas is prevented from impinging on the window by a double air curtain.

It has been realised that where a flow of clean air has been blown out of an aperture in front of a window and erratic opacity measurements have resulted this has been due at least in part to a flow of clean air into the exhaust gases, the opacity of which is being measured.

This is explained with reference to FIG. 1. A chamber 10 contains exhaust gases and is bounded by a wall 11. An optical path 12 through the chamber 10 passes through an aperture 13 in the wall 11. A second wall 14 parallel to the wall 11 includes a window 15 through which the optical path passes.

The parallel walls 11 and 14 define between them a passage 16 along which clean air is passed, the flow being along the passage 16 and through the aperture 13, as shown by the arrows.

Light generating or receiving apparatus (not shown) is situated behind the window 15.

In operation the opacity of the exhaust gases in the chamber 10 is measured by measuring the change in intensity of a light beam passing along the light path 12. The continuous flow of air out of the passage 16 through the aperture 13 sweeps away any exhaust gases in the clean air flow back into the chamber 10 before they can contaminate the window 15.

The standard method of testing exhaust emissions is the "free-acceleration" test in which the engine is allowed to idle and then the throttle is opened fully until the engines maximum speed is reached and then the throttle is closed and the engine allowed to return to idle. In the course of this cycle, the pressure of the exhaust gases varies greatly. It has been realised that if the pressure of the clean air is sufficient to prevent exhaust gases impinging on the window 15 when the exhaust gas pressure is high then when the exhaust gas pressure is low a plume 17 of clean air passes through the aperture 13 into the chamber 10. As a result the length of the optical path 12 which actually passes through the exhaust gases is reduced. This variation in path length with exhaust gas pressure produces erroneous opacity measurements.

BRIEF DESCRIPTION OF THE DRAWINGS

A sensor embodying the invention will now be described by way of example only with reference to the accompanying diagramatic Figures in which.

DETAILED DESCRIPTION

Figure 1:
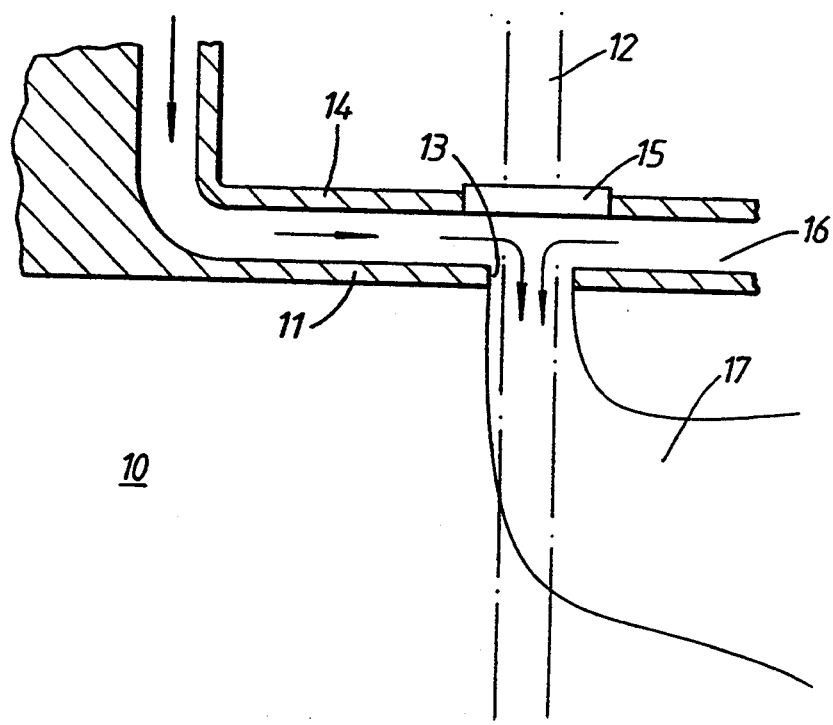
FIG. 1 is an explanatory diagram which shows a prior art system.
Figure 2:
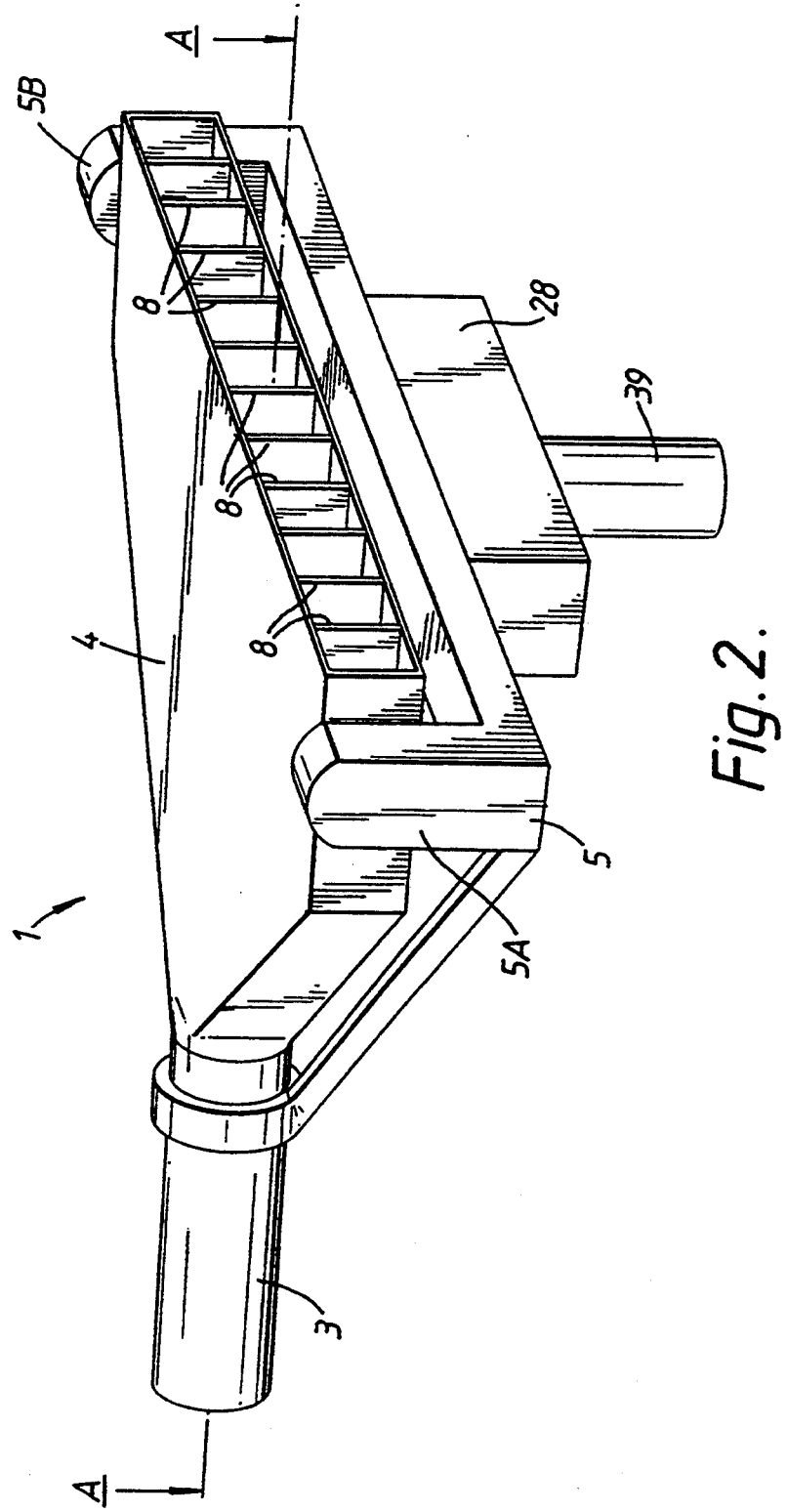
FIG. 2 shows a perspective view of a vehicle exhaust particle sensor according to the invention.
Figure 3:
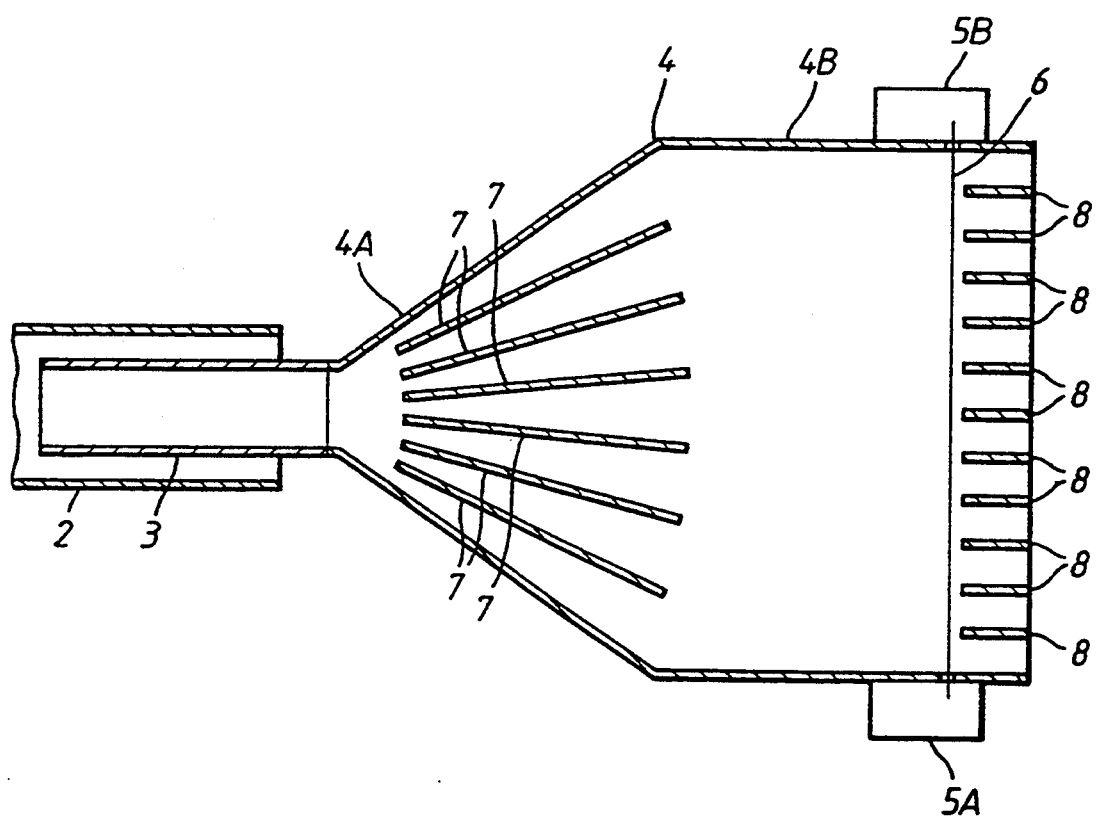
FIG. 3 shows a cross sectional view through the sensor of FIG. 2 along the line A—A in FIG. 2.
Figure 4:
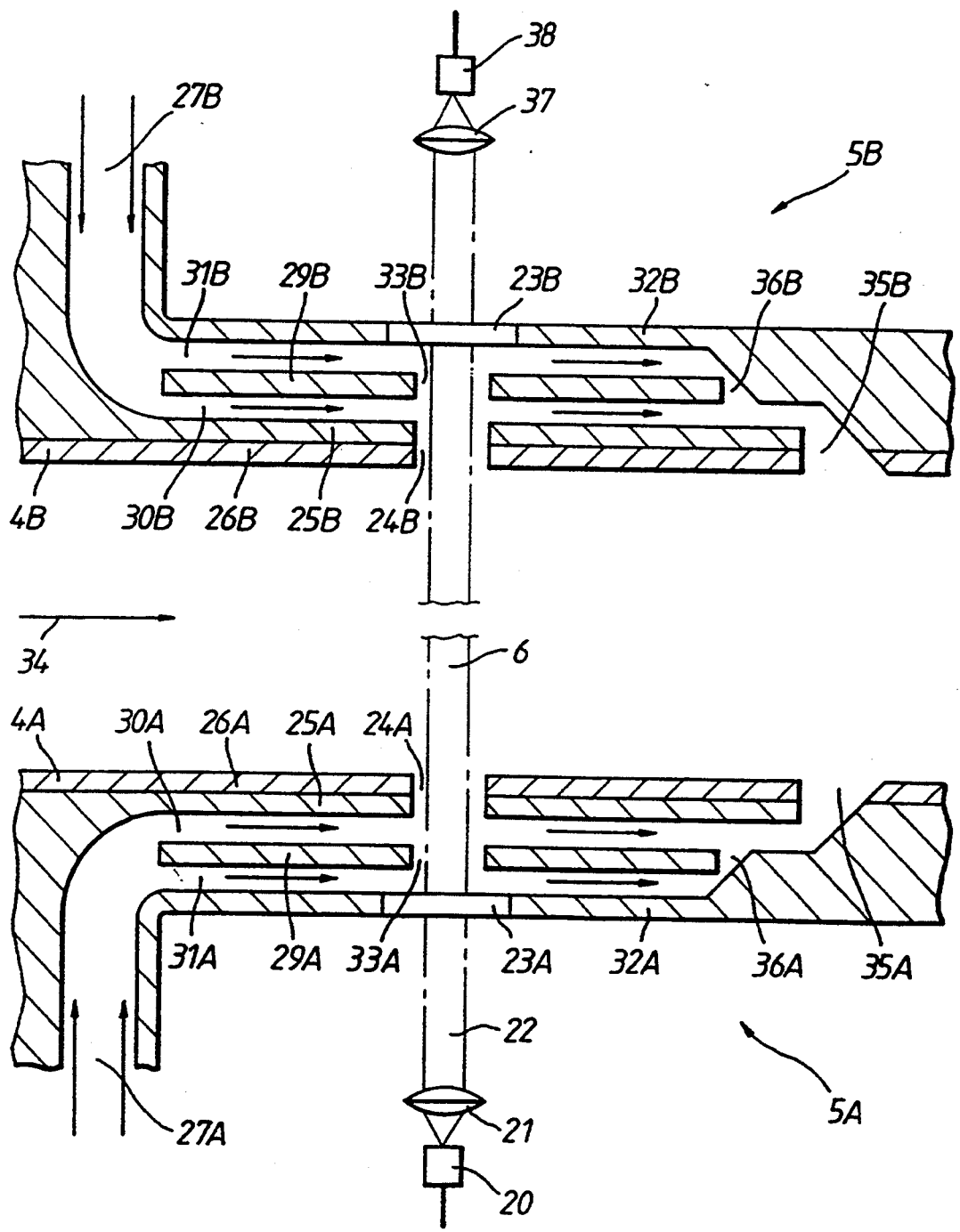
FIG. 4 shows a more detailed view of a part of the cross section of FIG. 3, identical parts having the same reference numerals throughout.

Referring to FIGS. 2 to 4 an exhaust gas particle sensor 1 is shown, this is intended to measure particle levels in exhaust gases from an exhaust pipe 2. The particle sensor 1 has three main parts, an input tube 3, a sensing portion 4 and a substantially 'U' shaped main body 5. The main body 5 is rigidly attached to the input tube 3, while the sensing portion 4 is releasably attached to the main body 5 and input tube 3.

The input tube 3 is circular and has a diameter of 25 mm so that, in use, it can be inserted into the end of a vehicle exhaust pipe 2. The narrowness of the input tube allows it to fit into a very wide range of sizes of exhaust pipe. Since the input tube 3 is placed inside the vehicle exhaust pipe 2 only undiluted exhaust gases are taken into the sensor 1.

The input tube 3 is rigid and passes far enough up the exhaust pipe 2 to prevent air being drawn in to dilute the exhaust gases. The sensor 1 is used adjacent the end of the exhaust pipe 2 to keep the input tube 3 relatively short and so reduce the tendency of particles in the exhaust gases to stick to the sides of the input tube 3 or agglomerate, both of which would tend to reduce the measured opacity of the exhaust gases.

The sensing portion 4 comprises a transition section 4A immediately downstream of the input tube 3 and a constant area portion 4B of rectangular cross section downstream of the transition section 4A. The constant area portion 4B forms a gas duct 100 mm wide and 10 mm high, that is a two fold increase in cross-sectional area over the input tube 3, and the transition section 4A forms a smooth transition between the input tube 3 and the constant area portion 4B. The opacity of the exhaust gases is measured as it passes through the constant area portion 4B. This arrangement is used because if the sensor had the same cross section throughout the small diameter of the input tube 3 would only give a very short optical path length for opacity measurement, by measuring opacity across the constant area portion 4B a quadrupled optical path length is provided.

The U shaped body 5 has two uprights 5A and 5B. Opacity measurement is carried out using a light beam produced within the upright 5A, passing through the constant area portion 4B and being received in the upright 5B along an optical path 6.

In the transition portion 4A a first plurality of baffles 7 are provided. The baffles 7 extend right across the transition portion 4A and modify the exhaust gas flow through the transition portion 4A so that the time taken for a wavefront in the exhaust gas to travel from the upstream end of the transition portion 4A to the optical path 6 is substantially a constant across the whole width of the exhaust gas flow. The time taken will of course vary depending on the pressure and flow rate of the exhaust gases, but the important thing is that at any given exhaust gas pressure the time taken is independent of position across the gas flow.

If the first baffles 7 were not provided, the velocity of gas in the central region of the transition portion 4A would be greater than at the edges so that if a pulse of smoke was present in the exhaust gases entering the transition portion 4A it would be spread out along the flow of exhaust gases resulting in a reduced opacity value as the smoke crosses the optical path 6.

The time taken is referred to as substantially constant since there will still be boundary layer effects at the edges of the transition portion 4A and the constant volume portion 4B, but the effect of these is insignificant compared to the effects that would be produced by the transition if the baffles 7 were not present.

A second set of 11 baffles 8 are provided downstream of the optical path 6 at the downstream end of the constant area portion 4B. These baffles extend across the constant area portion 4B and divide it into 12 parallel sided gas flow channels of equal size.

The baffles 8 prevent any wind past the sensor 1 blowing clean air into the constant area portion 4B and into the optical path 6. If this occurred it would of course make the opacity measurement unreliable.

The baffles 8 prevent such clean air entering the optical path 6 because they reduce the lateral dimension of any swirl generated by wind and so reduce the distance which any wind generated swirl will penetrate into the constant area portion 4B.

Referring to FIG. 4 the uprights 5A and 5B of the main body 5 are shown in more detail. Inside the upright 5A is a light emitter 20 and a lens 21 arranged to produce a light beam 22 which follows the light path 6. The light beam 22 passes through a protective window 23A in a wall 32A within the upright 5A and an aperture 24A in a wall 25A of the upright 5A and a wall 26A of the constant area portion 4B into the exhaust gases within the portion 4B.

In order to prevent particles from the exhaust gases being deposited on the window 23A a dual air curtain is provided. Clean air under pressure is provided along a clean air duct 27A. This air comes from a fan 28 and an electrostatic precipitator (not shown) which filters the air to remove any smoke and other particles in the ambient air before it is passed along the clean air duct 27A.

A wall 29A divides the clean air duct 27A into a first clean air passage 30A and a second clean air passage 31A, the first clean air passage 30A is defined between the wall 29A and the wall 25A while the second clean air passage 31A is defined between the wall 29A and the wall 32A. The wall 29A has an aperture 33A to allow the light beam 22 to pass through it.

The airflow along the two clean air passages 30A and 31A is parallel to the direction of flow of exhaust gases through the constant area portion 4B, denoted by the arrow 34. This parallel flow helps to reduce the tendency for clean air plumes to be injected into the constant area portion 4B. The two clean air passages 30A and 31A recombine downstream of the optical path 6 and the clean air flow is dumped into the exhaust gas flow through an opening 35A. Before the two clean air passages 30A and 31A recombine there is a constriction 36A in the second clean air passage 31A, so that the air pressure within the second clean air passage 31A is always greater than the air pressure within the second clean air passage 30A. As a result there is a pressure differential across the aperture 33A generating a flow of clean air from the second clean air passage 31A into the first clean air passage 30A. When there is a leakage of exhaust gases from the constant area portion 4B into the first clean air passage 30A the exhaust gases are prevented from reaching the window 23A by the higher pressure in the second clean air passage 31A and the exhaust gases are carried away down the first clean air passage 30A.

When the "free-acceleration" test is used the clean air pressure in the first clean air passage 30A need not be as high as in prior art clean air systems because some leakage of exhaust gases into the first clean air passage 30A can be tolerated when the engine is running at full speed and the exhaust gases are at a high pressure without any contamination of the window 23A. As a result when the engine is running at a lower speed or idling and the exhaust gas pressure is reduced it is less likely that clean air will escape into the constant volume portion 4B and produce a clean air plume along the optical path 6. Also, the first clean air passage 30A can be made very narrow because the second clean air passage 31A is acting as a back up to it, as a result the change in the length of the optical path 6 passing through exhaust gases due to penetration of the first clean air passage 30A by exhaust gases is small, reducing changes in the apparent opacity due to this change in path length.

A similar air curtain system, denoted by the letter B in FIG. 4, is used in the second upright 5B to prevent particle deposition on a window 23B. Behind the window 23B is a lens 37 arranged to focus the light beam 22 onto a photosensor 38.

By comparing the intensity of the light beam 22 incident on the photodetector 38 when exhaust gases are present in the chamber 10 with the intensity of the light beam 22 incident on the photodector 38 when only clean air is present in the chamber 10 the opacity of the gases along the optical path 6 within the constant area portion 4B can be calculated, as is known from patent application Ser. No. 9105731.

A handle 39 is secured to the main body 5 to allow the sensor 1 to be held in position with the input tube 3 inside a vehicle exhaust pipe 2. Power for the compressor 25, light emitter 20, photodetector 38 and associated electronics is provided by batteries attached to the main body 5. This allows the sensor i to be readily portable for spot-checks of vehicles, but if it is to be used in one place only a lead to plug into mains power could be used.

The sensing portion 4 of the particle sensor is located against the input tube 3 by a push fit seal formed by a resilient gasket, and is releasably attached to the main body 5 by two catches (not shown), one on each of the uprights 5A and 5B. This allows the sensing portion to be removed and replaced as needed in the event of damage or to allow cleaning out of soot deposited from the exhaust gases.

To allow calibration of the sensor 1 the sensing portion 4 can be removed and an optical filter having a known transmission coefficient can be placed in the light path 6.

It would also be possible to use a number of different sensing portions for different engines is this desirable if, for example, the differences in exhaust gas pressures would otherwise be too great for the sensor to cope with.

Since all of the optical components are housed in the main body 5 the removal and replacement of the sensing portion 4 for whatever reason will not necessitate the realignment or adjustment of any of the optical components.

The electrostatic precipitator could be replaced by any other filter type, such as a mesh filter, to remove particles from the air used in the air curtains. A remote air intake, for example on the end of a flexible hose attached to the sensor, could be used to reduce the filtering required by obtaining relatively clean air from a region away from the vehicle exhaust pipe. Alternatively where the sensor is used repeatedly in the same area, such as a testing station, the compressor and filter could be omitted from the sensor and clean compressed air supplied by a hose from a fixed remote compressor and filter.

The system described above has baffles 7 within the transition portion 4A only, it is equally possible to have the baffles continuing to the constant area portion 4B or starting in the inlet tube 3 if necessary. The exact configuration of baffles used will depend on the precise sizes and shapes of the inlet tube 3, transition portion 4A and constant area portion 4B.

In order to allow the sensing portion 4 to be removed, where the baffles 7 begin within the inlet tube 3 a part of the sensing portion 4 having the same diameter as the inlet tube 3 containing the baffles 7 will have to be fixed to the sensing portion 4 rather than the inlet tube 3.

In addition to the first baffles 7, obstructions could also be placed to slow the gas flow in the centre of the transition portion 4A.

The number of second baffles 8 used, and thus the number of seperate channels into which the outlet end of the constant area portion 4B is divided could be altered, depending on the width and length available and the degree of wind induced swirl expected.

In an alternative construction the two walls 25 and 26 could be replaced by one wall forming part of the sensing portion 4 and cooperating with the remaining walls which are part of the uprights 5 to form the clean air curtains.

It will be clear that there are many ways in which the walls defining the clean air passages can be divided between the sensing portion 4 and the uprights. One other preferred way is to have the windows 23 attached to the uprights 5 and all of the other parts of the clean air curtain arrangements attached to the sensing portion 4.

Instead of a double air curtain more layers of air curtain, such as a triple or quadruple air curtain, could be used.

Instead of removing the sensing portion 4 for calibration an optical filter having a known transmission coefficient can be placed in the light path 6 by inserting it between the second baffles 8.

Instead of a fan, any other form of air compressor could be used.

We claim:

1. An exhaust gas particle sensor comprising an inlet section, a transition section, an opacity measurement section terminating in an outlet, said sections being in gas flow series, the measurement section including means for measuring opacity along an optical path within said section, said section having a different cross section than the inlet section said optical path being transverse to the gas flow therethrough and means including a plurality of first baffles in the transition section for controlling exhaust gas flow such that the time taken for gas to travel from the inlet section to the measurement section is substantially independent of the position of the gas across the inlet section and the time taken for a wave front of gas to travel from the upstream portion of the transition section adjacent the inlet section to said optical path is constant across the width of the gas flow.

2. A sensor as claimed in claim 1 further comprising means including a plurality of second baffles arranged in the measurement section downstream of the optical path and arranged to divide the measurement section into a plurality of parallel gas flow channels at the outlet for preventing clean air being blown upstream from the outlet into the measurement section.

3. A sensor as claimed in claim 2 where a filter of known transmission coefficient can be inserted between the second baffles to calibrate the sensor.

4. A sensor as claimed in claim 1 where the opacity measurement section can be detached.

5. A sensor as claimed in claim 4 where a filter of known transmission coefficient can be used to replace the opacity measurement section to calibrate the sensor.

6. A sensor as claimed in claim 1 where the particles sensed are smoke particles.

7. An exhaust gas particle sensor including a measurement section where the sensor measures the opacity of the exhaust gas along steam passing therethrough said sensor acting along an optical path which extends across said stream and passes through a transparent window comprising: means for preventing the exhaust gas from impinging on the window including a double air curtain passing between said window and said exhaust gas stream in a direction parallel to said stream and perpendicular to said optical path.

8. A sensor as claimed in claim 7 where the air curtain has more than two layers.

9. A sensor as claimed in claim 8 where air used to produce the air curtain is cleaned by an electrostatic precipitator.

* * * * *